United States Patent [19]

Dozeman et al.

[11] Patent Number: 5,602,254

[45] Date of Patent: Feb. 11, 1997

[54] METHOD FOR MAKING QUINOLINE CARBOXYLIC ACIDS OR NAPHTHYRIDINE CARBOXYLIC ACIDS IN FREE BASE FORM

[75] Inventors: Gary J. Dozeman, Zeeland; Kenneth T. Porter; James N. Wemple, both of Holland, all of Mich.

[73] Assignee: Warner-Lambert Company, Morris Plains, N.J.

[21] Appl. No.: 452,208

[22] Filed: May 26, 1995

[51] Int. Cl.$^6$ .................. C07D 215/56; C07D 471/02
[52] U.S. Cl. .................................. 546/123; 546/156
[58] Field of Search ............................... 546/123, 156

[56] References Cited

U.S. PATENT DOCUMENTS

| | | | |
|---|---|---|---|
| 4,146,719 | 3/1979 | Irikura | 544/363 |
| 4,563,459 | 1/1986 | Grohe et al. | 514/254 |
| 4,771,054 | 9/1988 | Domagala et al. | 514/312 |
| 4,851,418 | 7/1989 | Sanchez | 514/300 |
| 4,867,901 | 9/1989 | Bosch et al. | 252/180 |
| 4,950,787 | 8/1990 | Griffith et al. | 562/583 |
| 4,973,590 | 11/1990 | Preiss et al. | 514/254 |
| 5,290,794 | 3/1994 | Mehta et al. | 514/300 |

OTHER PUBLICATIONS

Kirk–Othmer, Encyclopedia of Chem. Tech. 3ed., vol. 10, pp. 284–297 and pp. 489–499 (1980).

*Primary Examiner*—Bernard Dentz
*Attorney, Agent, or Firm*—Todd M. Crissey

[57] ABSTRACT

The present invention provides a method of making quinolone carboxylic acids or naphthyridine carboxylic acids in free base form, the method comprising dissolving a quinolone carboxylic acid salt or naphthyridine carboxylic acid salt in a solvent system to form a solution; combining the solution containing the quinolone carboxylic acid salt or naphthyridine carboxylic acid salt with a calcium salt in an amount in the range of about 0.01% to about 5.0% by weight of the quinolone carboxylic acid salt or naphthyridine carboxylic acid salt and a base, the combination resulting in the formation of a precipitate; and collecting the precipitate. Also provided is a solid bulk pharmaceutical chemical composition which is the product resulting from the precipitation.

18 Claims, No Drawings

METHOD FOR MAKING QUINOLINE CARBOXYLIC ACIDS OR NAPHTHYRIDINE CARBOXYLIC ACIDS IN FREE BASE FORM

FIELD OF THE INVENTION

This invention relates to a method of making quinolone carboxylic acids or naphthyridine carboxylic acids in free base form. This invention also relates to a solid bulk pharmaceutical composition containing a quinolone carboxylic acid or a naphthyridine carboxylic acid that is suitable for preparing parenteral formulations for use in the treatment of systemic bacterial infections.

BACKGROUND OF THE INVENTION

Quinolone carboxylic acids or naphthyridine carboxylic acids are used in the treatment of patients having various conditions. Most often, quinolone carboxylic acids or naphthyridine carboxylic acids are used as anti-infective agents. The term "patient" means humans and other animals.

One way to deliver quinolone carboxylic acids or naphthyridine carboxylic acids to a patient is via a parenteral route. For example, a suitable solution of or a suitable formulation containing the quinolone carboxylic acid or naphthyridine carboxylic acid compounds can be injected into muscle tissue or the blood stream.

Formulation of parenteral dosage forms of quinolone carboxylic acids or naphthyridine carboxylic acids typically starts with the corresponding bulk drug substance prepared in its free base form. Chemical synthesis of the free base form of the quinolone carboxylic acids or naphthyridine carboxylic acids often involves hydroxide ion induced neutralization of an acid salt derivative of the quinolone carboxylic acid or naphthyridine carboxylic acid.

Poor filtration rates during the processing of bulk drug substances can cause major product quality problems including increased difficulties in washing out low level impurities from the product. In addition, when slow, inefficient filtration occurs, it is often necessary to use rework procedures to assure a thorough wash of the product.

Longer filtration times or rework procedures should be avoided because they result in increased time of exposure of the product to the environment and a corresponding greater chance for biological contamination of the product. Furthermore, a slow filtration procedure will normally add additional cost to the product because additional processing time requires extra labor. Moreover, these problems are magnified upon scale-up to commercial quantities.

The present invention provides a method of making quinolone carboxylic acids or naphthyridine carboxylic acids in free base form that provides for dramatically improved filtration rates. The present invention uses trace levels of calcium (II) salts, which results in products having improved filtration rates.

SUMMARY OF THE INVENTION

The present invention provides a method of making quinolone carboxylic acids or naphthyridine carboxylic acids in free base form, the method comprising dissolving a quinolone carboxylic acid salt or naphthyridine carboxylic acid salt in a solvent system to form a solution; combining the solution containing the quinolone carboxylic acid salt or naphthyridine carboxylic acid salt with a calcium salt in an amount in the range of about 0.01% to about 5.0% by weight of the quinolone carboxylic acid salt or naphthyridine carboxylic acid salt and a base, the combination resulting in the formation of a precipitate; and collecting the precipitate.

In a preferred embodiment, the present invention provides a method of making the free base form of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid, the method comprising dissolving the hydrochloride salt of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino)pyrrolidin-1-yl]-1-cyclopropyl-6-fluoro-1,4-dihydro-4-oxo-1,8-naphthyridine-3-carboxylic acid in a solvent system to form a first solution; adding a calcium salt to a solvent system in an amount in the range of about 0.01% to about 5.0% by weight of the hydrochloride salt of the quinolone or naphthyridine to form a second solvent system; combining the first solvent system and the second solvent system while simultaneously adding a base such that the pH of the resulting mixture is kept in the range of about 6.5 to about 8.0 at a temperature in the range of about 50° C. to about 70° C., which results in the formation of a precipitate; and collecting the precipitate.

Also provided is a solid bulk pharmaceutical chemical composition comprising 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino)pyrrolidin-1-yl]-1-cyclopropyl-6-fluoro-1,4-dihydro-4-oxo-1,8-naphthyridine-3-carboxylic acid; and calcium in an amount in the range of about 0.001% to about 1.0% by weight of the 7-(3-amino-1pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid.

DETAILED DESCRIPTION OF THE INVENTION

The present invention provides a method of making quinolone carboxylic acids or naphthyridine carboxylic acids in free base form, the method comprising dissolving a quinolone carboxylic acid salt or naphthyridine carboxylic acid salt in a solvent system to form a solution; combining the solution containing the quinolone carboxylic acid salt or naphthyridine carboxylic acid salt with (1) a calcium salt in an amount in the range of about 0.01% to about 5.0% by weight of the quinolone carboxylic acid salt or naphthyridine carboxylic acid salt, and (2) approximately one equivalent of a base, the combination resulting in the formation of a precipitate; and collecting the precipitate.

The solvent system used to dissolve the quinolone carboxylic acid salt or naphthyridine carboxylic acid salt may comprise one or more solvents. In a preferred embodiment, the solvent system comprises water and methanol in a volume to volume ratio of about 1:5 water to methanol. In general, any solvent system in which the quinolone carboxylic acid salt or naphthyridine carboxylic acid salt will dissolve can be used. However, the solvents that make up the solvent system should be compatible with the quinolone carboxylic acid salt or naphthyridine carboxylic acid salt. Moreover, in order to dissolve the quinolone carboxylic acid salt or naphthyridine carboxylic acid salt, it may be necessary to heat the solvent system. When water is used as a solvent, preferably the water is water for injection (WFI) or demineralized water that has been further purified by reverse osmosis or ultrafiltration.

A calcium salt is combined with the solution formed upon the dissolution of the quinolone carboxylic acid salt or naphthyridine carboxylic acid salt in the solvent system. The calcium salt can be added directly as a solid. Alternatively, the calcium salt can be combined as part of a solution. For example, the calcium salt can be added to a solvent system and the solvent system containing the calcium salt combined with the solvent system containing the dissolved quinolone carboxylic acid salt or naphthyridine carboxylic acid salt.

In general, the solvent system into which the calcium salt is added has the same properties as the solvents which may be used to dissolve the quinolone carboxylic acid salt or naphthyridine carboxylic acid salt. In a preferred embodiment, the calcium salt is added to water.

The amount of the calcium salt required in order to provide for increased filtration rates is in the range of about 0.01% to about 5.0% by weight of the quinolone carboxylic acid salt or naphthyridine carboxylic acid salt. In a preferred embodiment, the amount of the calcium salt is in the range of about 0.02% to about 2.0%. In a more preferred embodiment, the calcium salt is in the range of about 0.1% to about 1.0%.

The calcium salt can be any salt of calcium that is not detrimental to the patient to which the quinolone carboxylic acid or naphthyridine carboxylic acid is to be administered. Representative examples of calcium salts that may be used in the present invention are calcium hydroxide, calcium chloride, calcium oxide, calcium sulfate and calcium phosphate. A preferred calcium salt is calcium hydroxide.

The solution containing the quinolone carboxylic acid salt or naphthyridine carboxylic acid salt is neutralized by the addition of approximately one equivalent of a base with respect to the carboxylic acid salt, which results in the free base form of the quinolone carboxylic acid or naphthyridine carboxylic acid precipitating from the solution.

Various modes of combination of the quinolone carboxylic acid salt or naphthyridine carboxylic acid salt with the base and the calcium salt can be used in the present invention. In a preferred mode of combination, a quinolone carboxylic acid salt or naphthyridine carboxylic acid salt solution and a separate solution of the base are added simultaneously to a solution containing the calcium salt.

In another mode of combination, the neutralization is accomplished by adding a base to the solution containing the quinolone carboxylic acid salt or naphthyridine carboxylic acid salt and the calcium salt. Alternatively, the calcium salt may be added to the base and then the solution containing the base and the calcium salt added to the solution containing the quinolone carboxylic acid salt or naphthyridine carboxylic acid salt.

In another embodiment of the present invention, the solution containing the calcium salt is added to the solution containing the quinolone carboxylic acid salt or naphthyridine carboxylic acid salt at the same time that the solution is neutralized. In other words, the base is added concurrently with the calcium salt. The calcium salt may be added to the solution containing the quinolone carboxylic acid salt or naphthyridine carboxylic acid salt as a solid, as part of a separate solution or in the same solution as the base. Other modes of combination are apparent to those skilled in the art, and all are contemplated as falling within the scope of the present invention.

Any base known to those skilled in the art can be used to neutralize the solution containing the quinolone carboxylic acid salt or naphthyridine carboxylic acid salt. Preferably, the base is sodium hydroxide. More preferably, the base is an aqueous 5% w/w sodium hydroxide solution.

In a preferred embodiment, the pH of the solution containing the quinolone carboxylic acid salt or naphthyridine carboxylic acid salt is kept during the neutralization step in the range of about 6.5 to about 8.0 at a temperature in the range of about 50° C. to about 70° C. Preferably, the pH is kept in the range of about 6.7 to about 7.7 in this temperature range.

After neutralization, the precipitate that is formed is collected. Typically, the precipitate is collected by filtering it from the liquid portion of the solution. For example, the precipitate may be collected by filtration using a Buchner funnel, or on large scale, the precipitate may be filtered using a centrifuge. The collected precipitate is then dried to yield the free base form of the desired quinolone carboxylic acid or naphthyridine carboxylic acid.

The quinolone carboxylic acid salt or naphthyridine carboxylic acid salt can be any salt of a quinolone carboxylic acid or a naphthyridine carboxylic acid that is known to those skilled in the art. Examples of suitable salts include the phosphate, sulfate and carboxylate salts, such as an acetate salt. Preferably, however, the salt is the hydrochloride salt.

The quinolone carboxylic acids or naphthyridine carboxylic acids of the present invention have an amino group, which can be obtained by the present method in the free base form. The method of the present invention can be used to obtain the free base form of any such quinolone carboxylic acid or naphthyridine carboxylic acid known to those skilled in the art. Examples of quinolone carboxylic acids or naphthyridine carboxylic acids which can be used in the present invention include, but are not limited to, the quinolone carboxylic acids or naphthyridine carboxylic acids disclosed in U.S. Pat. No. 4,851,418 (to Sanchez); U.S. Pat. No. 4,563,459 (to Grohe, et al.); U.S. Pat. No. 4,146,719 (to Irikura); and U.S. Pat. No. 4,771,054 (to Domagala, et al.), the disclosures of which are hereby incorporated by reference. A preferred quinolone carboxylic acid is 7-(3-amino-1-pyrrolidinyl)-8-chloro-1-cyclopropyl -6fluoro-1,4-dihydro -4-oxoquinoline-3-carboxylic acid. A preferred naphthyridine carboxylic acid is 7-[3-S-(2S-aminopropionylamino) pyrrolidin-1-yl]-1-cyclopropyl -6-fluoro-1,4-dihydro-4-oxo-1,8-naphthyridine-3-carboxylic acid.

Also contemplated is a method of making the free base form of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid, the method comprising dissolving the hydrochloride salt of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid in a solvent system to form a first solution; adding a calcium salt to a solvent system in an amount in the range of about 0.01% to about 5.0% by weight of the hydrochloride salt of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino)pyrrolidin-1-yl]-1-cyclopropyl-6-fluor-1,4-dihydro-4-oxo-1,8-naphthyridine-3-carboxylic acid to form a second solvent system; combining the first solvent system and the second solvent system while simultaneously adding a base such that the pH of the resulting mixture is kept in the range of about 6.5 to about 8.0 at a temperature in the range of about 50° C. to about 70° C., which results in the formation of a precipitate; and collecting the precipitate.

The present invention also provides for a solid bulk pharmaceutical chemical composition, the composition comprising 7-(3-amino-1-pyrrolidinyl)-8-chloro-1-cyclopropyl-6- fluoro-1,4-dihydro-4-oxoquinoline-3-carboxylic acid or 7-[3-S-(2-S-aminopropionylamino) pyrrolidin-1-yl] -1-cyclopropyl-6-fluoro-1,4-dihydro-4-oxo-1,8-naphthyridine-3-carboxylic acid; and calcium in an amount in the range of 0.001% to about 1.0% by weight of the 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid.

Preferably, the calcium is present in an amount in the range of about 0.005% to about 0.5% by weight of the 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino)pyrrolidin-1-yl]-1-cyclopropyl-6-fluoro-1,4-dihydro-4-oxo-1,8-naphthyridine-3-carboxylic acid. More preferably, the calcium is present in an amount in the range of about 0.01% to about 0.1% by weight of the 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl] -1-cyclopropyl-6-fluoro-1,4-dihydro-4-oxo-1,8-naphthyridine-3-carboxylic acid.

The solid bulk pharmaceutical chemical composition is intended for use as the active ingredient in the preparation of parenteral dosage forms in the treatment of systemic bacterial infections.

The examples presented below are intended to illustrate particular embodiments of the invention and are not intended to limit the scope of the specification, including the claims, in any manner.

EXAMPLES

Particle Size Analysis

Particle size was determined by image analysis using a Quantimet 520 image analyzer made by Leica, Inc., Deerfield, Ill.

A sample (ca. 20 mg) of the quinolone or naphthyridine bulk pharmaceutical chemical was dispersed in approximately 3 mL of 1.300 refractive index oil, series AAA (R. P. Cargille, Cedar Cove, N.J.). One or two drops of this dispersion was transferred to a microscope slide using a wide bore transfer pipet, and a cover slide was placed over the sample. Using a calibrated microscope (stage micrometer), the sample was measured using a QBASIC program employing software obtained with the Quantimet 520 image analyzer from Leica, Inc. based on the objective selected and the grey scale chosen for detection. Magnification was chosen so that the largest observed particle was slightly smaller than the measured frame. The number of particles varies with particle size but normally >600 and <2500 particles were measured. No more than 250 particles were detected per field. The raw data was stored on an optical disk drive and a Quattro Pro macro program was used to generate the particle size report.

$$\text{Number Average Particle Size} = \frac{\sum_{i=1}^{n} L_i}{n}$$

$$90\%>, 90\%<, \text{Volume Average Size} = \frac{\sum_{i=1}^{n} L_i V_i}{\sum_{i=1}^{n} V_i}$$

and $$\text{Aspect Ratio} \left( \frac{\sum_{i=1}^{n} \frac{L_i^2}{A_i}}{n} \right)$$

where $L_i$=maximum feret diameter for each particle (measured for each particle);

n=Number of particles measured;

$A_i$=Area of each particle (measured by software for each detected particle); and $V_i$=volume of each particle estimated from $A_i^2/L_i$.

Calcium Analysis

The percent calcium in a sample was measured by atomic absorption using a Model Video 11 AA/AE Spectrophotometer from Instruments Labs, Inc., Andover, Me.

Example 1

7-(3-Amino-1-pyrrolidinyl)-8-chloro-1-cyclopropyl-6-fluoro-1,4-dihydro-4-oxoquinoline-3-carboxylic acid

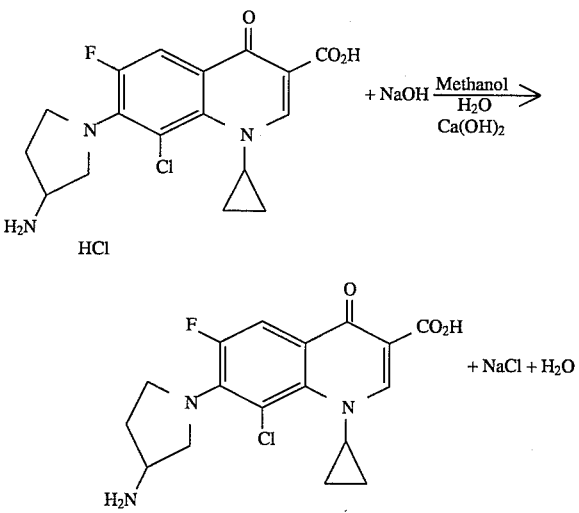

To a 1-liter flask was charged 100 g (0.27 mol) 7-(3-amino-1-pyrrolidinyl)-8-chloro-1-cyclopropyl-6-fluoro-1,4-dihydro-4-oxoquinoline-3-carboxylic acid monohydrochloride followed by 200 mL methanol and 200 mL demineralized water. The mixture was stirred and heated to 60° C. where it was maintained until solution was achieved. To a separate 1-liter flask was added 0.5 g $Ca(OH)_2$ and 200 mL demineralized water and the mixture stirred and heated to 60° C. To this mixture was simultaneously added the solution containing the 7-(3-amino-1-pyrrolidinyl)-8-chloro-1-cyclopropyl-6-fluoro-1,4-dihydro-4-oxoquinoline-3carboxylic acid monohydrochloride in aqueous methanol while at the same time charging 5% w/w NaOH at such a rate to maintain the pH between 7.5 and 8.0. When the addition was complete, the mixture was stirred and cooled to 25° C. over 1 hour and filtered on a 4 inch Buchner funnel (filtration time: 38 seconds) and the solid washed with 200 mL demineralized water to give a wet cake. The cake was vacuum dried to give 7-(3-amino-1-pyrrolidinyl)-8-chloro-1-cyclopropyl-6-fluoro-1,4-dihydro-4-oxoquinoline-3-carboxylic acid as a white solid (90 g).

Image analysis particle size results for wet cake: Number average size (magnification: 5×): 48μ; with 90%<77μ; and 90%>19μ. Water content for dried material: 5.1%; Image analysis particle size results for dried material (Quantimet 520, all samples dispersed in 1.300 RI oil—R. G. Cargille Co.): Number average size (magnification: 5×): 37μ; with 90%<61μ; and 90%>11μ. Calcium content: 0.06%; the reaction slurry before filtration was very fluid. The wet cake was coarse and crumbly. The dried product was powdery and free flowing.

The above experiment was repeated with the Ca(OH)₂ omitted to give 7-(3-amino-1-pyrrolidinyl)-8-chloro-1-cyclopropyl-6-fluoro-1,4-dihydro-4-oxoquinoline-3carboxylic acid as a white solid (88 g): Filtration time: 14 minutes and 30 seconds. Image analysis particle size results for wet cake: Number average size (magnification: 10×): 11μ; with 90%<20μ; and 90%>5μ. Water content for dried material: 2.9%; Image analysis particle size results for dried material: Number average size (magnification: 5×): 22μ; with 90%<40μ; and 90%>11μ. The reaction slurry was very thick on formation and caused agitation problems. The wet cake was very fine and slimy. Some fines passed through the filter. The dried product was hard, rubbery, and difficult to pulverize.

Example 2

7-[3-S-(2-S-Aminopropionylamino)pyrrolidin-1-yl]-1-cyclopropyl-6-fluoro-1,4-dihydro-4-oxo-1,8-naphthyridine-3-carboxylic acid

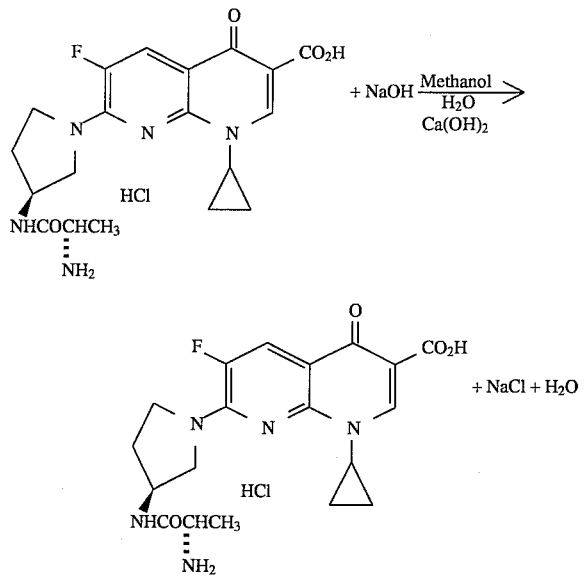

To a 1-liter flask was charged 100 g (0.27 mol) 7-[3-S-(2-S-aminopropionylamino)pyrrolidin-1-yl]-1-cyclopropyl-6-fluoro-1,4-dihydro-4-oxo-1,8-naphthyridine-3-carboxylic acid hydrochloride followed by 200 mL methanol and 200 mL demineralized water. The mixture was stirred and heated to 60° C., where it was maintained until solution was achieved. To a separate 1-liter flask was added 0.5 g Ca(OH)₂ and 200 mL demineralized water and the mixture stirred and heated to 60° C. To this mixture was simultaneously added the solution containing the 7-[3-S-(2-S-aminopropionylamino) pyrrolidin-1-yl]-1-cyclopropyl-6-fluoro-1,4-dihydro-4-oxo-1,8-naphthyridine-3-carboxylic acid hydrochloride in aqueous methanol, while at the same time charging 5% w/w NaOH at such a rate to maintain the pH between 7.5 and 8.0. When the addition was complete, the mixture was stirred and cooled to 25° C. over 1 hour and filtered on a 4 inch Buchner funnel (filtration time: 39 seconds) and the solid washed with 200 mL demineralized water to give the wet cake. The cake was vacuum dried to give 7-[3-S-(2-S-aminopropionylamino) pyrrolidin-1-yl]-1-cyclopropyl-6-fluoro-1,4-dihydro-4-oxo-1,8-naphthyridine-3-carboxylic acid as a white solid (87.8 g). Water content for dried material: 2.1%; Image analysis particle size results for dried material (Quantimet 520): Number average size (magnification: 5×): 53μ; with 90%<77μ; and 90%>29μ. Calcium content: 0.06%. The reaction slurry before filtration was very fluid. The wet cake was coarse and crumbly. The dried product was powdery and free flowing.

The above experiment was repeated with the Ca(OH)₂ omitted to give 7-[3-S-(2-S-aminopropionylamino) pyrrolidin-1-yl]-1-cyclopropyl-6-fluoro-1,4-dihydro-4-oxo-1,8-naphthyridine-3-carboxylic acid as a white solid (88.1 g): Filtration time: 5 minutes and 30 seconds. Water content for dried material: 2.7%; Image analysis particle size results for dried material: Number average size (magnification: 5×): 21μ; with 90%<37μ; and 90%>11μ. The reaction slurry was very thick on formation but thinned slightly over time. The wet cake was very fine and slimy. The dried product was hard, rubbery, and difficult to pulverize.

Example 3

7-(3-Amino-1-pyrrolidinyl)-8-chloro-1-cyclopropyl-6-fluoro-1,4-dihydro-4-oxoquinoline-3-carboxylic acid To a 100 gallon still was charged 38.0 kg (94.0 mol correcting for 0.38% ethanol and 0.10% water) 7-(3-amino-1-pyrrolidinyl)-8-chloro-1-cyclopropyl-6-fluoro-1,4-dihydro-4-oxoquinoline-3-carboxylic acid monohydrochloride followed by 3.0 kg carbon pitt PWA, 72 L methanol and 48 L (0.2 micron Posidyne filtered) demineralized water under a nitrogen atmosphere. The mixture was stirred and heated to 55° C. to 65° C. where it was maintained for 20 to 60 minutes before filtering through a Niagara followed by a 0.2 micron Ultipor Pall filter into a second 100 gallon still containing 76 g calcium hydroxide and 96 L filtered demineralized water with simultaneous addition of 75 kg filtered 5% sodium hydroxide in water (prepared by mixing 11.0 kg sodium hydroxide, 50% aqueous solution with 100 L filtered, demineralized water). Both acid and base solutions were metered into the second still at such a rate to maintain the pH between 6.7 and 7.7 and the batch temperature between 55° C. and 65° C. The first 100 gallon still and filters were rinsed with a mixture of 20 L filtered, demineralized water and 20 L methanol and the rinse added to the filtrate in the second 100 gallon still. The mixture was cooled to 20° C. to 30° C. (In some cases, further adjustment of the pH with small amounts of 37% hydrochloric acid or small amounts of 5% sodium hydroxide may be necessary in order to reach the desired pH value of 7.3 to 8.3 after allowing the mixture to cool to about room temperature.) The mixture was filtered on a centrifuge to collect the product. The product washed on the centrifuge with 200 L filtered, demineralized water and then vacuum dried at 20° C. to 50° C. to a water content of 11.9%. The dried product was milled using a Fitz mill equipped with a 2Å screen (0.093 inches) to give 35.9 kg of 7-(3-aminopyrrolidin-1-yl)-8-chloro-1-cyclopropyl-6-fluoro-1,4-dihydro-4-oxoquinoline-3carboxylic acid as a light tan solid (86.5 mol corrected for 11.9% water, 92% yield). Calcium content: 0.02%.

We claim:

1. A method of making quinolone carboxylic acids or naphthyridine carboxylic acids in free base form, the method comprising:
   a. Dissolving a quinolone carboxylic acid salt or naphthyridine carboxylic acid salt in a solvent system to form a solution;
   b. Combining the solution containing the quinolone carboxylic acid salt or naphthyridine carboxylic acid salt with a calcium salt in an amount in the range of about 0.01% to about 5.0% by weight of the quinolone carboxylic acid salt or naphthyridine carboxylic acid salt and a base, the combination resulting in the formation of a precipitate; and
   c. Collecting the precipitate.

2. The method of claim 1 wherein the calcium salt is combined in an amount in the range of about 0.02% to about 2.0% by weight of the quinolone carboxylic acid salt or naphthyridine carboxylic acid salt.

3. The method of claim 1 wherein the calcium salt is combined in an amount in the range of about 0.1% to about 1.0% by weight of the quinolone carboxylic acid salt or naphthyridine carboxylic acid salt.

4. The method of claim 1 wherein the solvent system comprises water and methanol.

5. The method of claim 1 wherein the quinolone carboxylic acid salt or naphthyridine carboxylic acid salt is in the form of a hydrochloride salt.

6. The method of claim 1 wherein the calcium salt is calcium hydroxide.

7. The method of claim 1 wherein the base is sodium hydroxide.

8. The method of claim 1 wherein the quinoline carboxylic acid is 7-(3-amino-1-pyrrolidinyl)-8-chloro-1-cyclopropyl-6-fluoro-1,4-dihydro-4-oxoquinoline-3-carboxylic acid.

9. The method of claim 1 wherein the naphthyridine carboxylic acid is 7-[3-S-(2-S-aminopropionyl amino)pyrrolidin-1-yl]-1-cyclopropyl-6-fluoro-1,4-dihydro-4-oxo-1,8-naphthyridine-3-carboxylic acid.

10. The method of claim 1 wherein the pH is kept in the range of about 6.5 to about 8.0 and the temperature in the range of about 50° C. to about 70° C., while the base is combined with the solution containing the quinolone carboxylic acid salt or naphthyridine carboxylic acid salt.

11. The method of claim 1 wherein the solution containing the quinolone carboxylic acid salt or naphthyridine carboxylic acid salt, the calcium salt, and the base are combined simultaneously.

12. A method of making the free base form of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid, the method comprising:
   a. Dissolving the hydrochloride salt of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionyl amino)pyrrolidin-1-yl]-1-cyclopropyl-6-fluoro-1,4-dihydro-4-oxo-1,8-naphthyridine-3-carboxylic acid in a solvent system to form a first solution;
   b. Adding a calcium salt to a solvent system in an amount in the range of about 0.01% to about 5.0% by weight of the hydrochloride salt of 7-(3-amino-1-pyrrolidinyl)-8-chloro-1-cyclopropyl-6-fluoro-1,4-dihydro-4-oxoquinoline-3-carboxylic acid or 7-[3-S-(2-S-aminopropionylamino) pyrrolidin-1-yl]-1-cyclopropyl-6-fluoro-1,4-dihydro-4-oxo-1,8-naphthyridine-3-carboxylic acid to form a second solvent system;
   c. Combining the first solvent system and the second solvent system while simultaneously adding a base such that the pH of the resulting mixture is kept in the range of about 6.5 to about 8.0 at a temperature in the range of about 50° C. to about 70° C., which results in the formation of a precipitate; and
   d. Collecting the precipitate.

13. The method of claim 12 wherein the calcium salt is added in an amount in the range of about 0.02% to about 2.0% by weight of the quinolone carboxylic acid salt or naphthyridine carboxylic acid salt.

14. The method of claim 12 wherein the calcium salt is added in an amount in the range of about 0.1% to about 1.0% by weight of the quinolone carboxylic acid salt or naphthyridine carboxylic acid salt.

15. The method of claim 12 wherein the calcium salt is calcium hydroxide.

16. The method of claim 12 wherein the base is sodium hydroxide.

17. The method of claim 12 wherein the first solution comprises methanol and water.

18. The method of claim 12 wherein the second solvent system comprises water.

* * * * *